United States Patent
Betelia et al.

(10) Patent No.: US 6,945,989 B1
(45) Date of Patent: Sep. 20, 2005

(54) APPARATUS FOR DELIVERING ENDOLUMINAL PROSTHESES AND METHODS OF MAKING AND USING THEM

(75) Inventors: Rainier Betelia, San Jose, CA (US); Edward M Gillis, Cupertino, CA (US); Jonathan M. Rourke, Los Altos, CA (US); Yi Yang, San Francisco, CA (US)

(73) Assignee: Endotex Interventional Systems, Inc., Cupertino, CA (US)

( * ) Notice: Subject to any disclaimer, the term of this patent is extended or adjusted under 35 U.S.C. 154(b) by 638 days.

(21) Appl. No.: 09/664,970

(22) Filed: Sep. 18, 2000

(51) Int. Cl.⁷ .................................. A61F 2/06
(52) U.S. Cl. ..................................... 623/1.11
(58) Field of Search .............................. 623/1.11, 1.12, 623/1.23, 1.2, 1.18, 1.34, 1.19; 606/108, 606/194

(56) References Cited

U.S. PATENT DOCUMENTS

| | | |
|---|---|---|
| 3,204,635 A | 9/1965 | Voss et al. |
| 3,485,234 A | 12/1969 | Stevens |
| 3,585,707 A | 6/1971 | Stevens |
| 3,760,808 A | 9/1973 | Bleuer |
| 4,023,559 A | 5/1977 | Gaskell |
| 4,424,054 A | 1/1984 | Conn et al. |
| 4,516,972 A | 5/1985 | Samson |
| 4,681,110 A | 7/1987 | Wiktor |
| 4,817,613 A | 4/1989 | Jaraczewski et al. |
| 4,842,590 A | 6/1989 | Tanabe et al. |
| 4,848,343 A | 7/1989 | Wallsten et al. |
| 5,019,090 A | 5/1991 | Pinchuk |
| 5,037,329 A | 8/1991 | Hillstead |
| 5,041,126 A | 8/1991 | Gianturco |
| 5,057,092 A | 10/1991 | Webster, Jr. |
| 5,089,006 A | 2/1992 | Stiles |
| 5,104,339 A | 4/1992 | Lazarus |
| 5,147,385 A | 9/1992 | Beck et al. |
| 5,158,548 A | 10/1992 | Lau et al. |
| 5,192,297 A | 3/1993 | Hull |
| 5,201,901 A | 4/1993 | Harada et al. |
| 5,242,399 A | 9/1993 | Lau et al. |
| 5,246,421 A | 9/1993 | Saab |
| 5,254,107 A | 10/1993 | Soltesz |
| 5,279,596 A | 1/1994 | Castaneda et al. |
| 5,290,295 A * | 3/1994 | Querals et al. .............. 604/264 |
| 5,290,310 A | 3/1994 | Makower et al. |

(Continued)

OTHER PUBLICATIONS

EPO Publication No. EP O 873 733 A1, "Controllable Stent Delivery System", Oct. 28, 1998.

(Continued)

Primary Examiner—(Jackie) Tan-Uyen T. Ho
(74) Attorney, Agent, or Firm—Orrick Herrington & Sutcliffe, LLP

(57) ABSTRACT

An apparatus for delivering a stent into a blood vessel includes a sheath having a rounded bullet-shaped distal portion including a plurality of flexible leaflets integrally molded thereto. The stent is disposed in its contracted condition within a lumen of the sheath proximate the distal portion. A bumper is slidably disposed within the lumen that includes a helical compression coil, a bumper element attached to the helical coil including a blunt distal edge for abutting the stent, and an extension element extending distally from the bumper element through the stent and between the leaflets to facilitate introducing the apparatus over a guidewire. The sheath is formed by inserting a bullet into a blunt-ended tube, and inserting the tube into a bullet-shaped bore in a heated die until the tube material is softened and deforms into a rounded bullet shape. Slits are then cut into the distal portion to create the leaflets.

13 Claims, 4 Drawing Sheets

U.S. PATENT DOCUMENTS

| | | | | |
|---|---|---|---|---|
| 5,312,415 | A | 5/1994 | Palermo | |
| 5,360,401 | A | 11/1994 | Turnland et al. | |
| 5,391,172 | A | 2/1995 | Williams et al. | |
| 5,395,308 | A | 3/1995 | Fox et al. | |
| 5,433,723 | A | 7/1995 | Lindenberg et al. | |
| 5,443,457 | A | 8/1995 | Ginn et al. | |
| 5,453,090 | A | 9/1995 | Martinez et al. | |
| 5,458,605 | A | 10/1995 | Klemm | |
| 5,460,608 | A * | 10/1995 | Lodin et al. | 604/103.09 |
| 5,484,425 | A | 1/1996 | Fischell et al. | |
| 5,554,139 | A | 9/1996 | Okajima | |
| 5,593,412 | A | 1/1997 | Martinez et al. | |
| 5,601,568 | A | 2/1997 | Chevillon et al. | |
| 5,630,801 | A | 5/1997 | Roussigne et al. | |
| 5,662,703 | A * | 9/1997 | Yurek et al. | 606/194 |
| 5,669,936 | A | 9/1997 | Lazarus | |
| 5,674,208 | A | 10/1997 | Berg et al. | |
| 5,683,451 | A | 11/1997 | Lenker et al. | |
| 5,693,086 | A | 12/1997 | Goicoechea et al. | |
| 5,695,499 | A | 12/1997 | Helgerson et al. | |
| 5,697,948 | A | 12/1997 | Marin et al. | |
| 5,700,269 | A | 12/1997 | Pinchuk et al. | |
| 5,702,418 | A | 12/1997 | Ravenscroft | |
| 5,704,926 | A | 1/1998 | Sutton | |
| 5,707,376 | A | 1/1998 | Kavteladze et al. | |
| 5,759,186 | A | 6/1998 | Bachmann et al. | |
| 5,772,669 | A | 6/1998 | Vrba | |
| 5,782,855 | A * | 7/1998 | Lau et al. | 604/164.13 |
| 5,788,707 | A | 8/1998 | Del Toro et al. | |
| 5,800,517 | A * | 9/1998 | Anderson et al. | 604/171 |
| 5,814,062 | A * | 9/1998 | Sepetka et al. | 606/198 |
| 5,824,041 | A * | 10/1998 | Lenker et al. | 606/195 |
| RE35,988 | E | 12/1998 | Winston et al. | |
| 5,868,755 | A | 2/1999 | Kanner et al. | |
| 5,891,090 | A * | 4/1999 | Thornton | 604/103.09 |
| 5,906,619 | A | 5/1999 | Olson et al. | |
| 5,935,135 | A * | 8/1999 | Bramfitt et al. | 606/191 |
| 6,019,778 | A | 2/2000 | Wilson et al. | |
| 6,024,763 | A * | 2/2000 | Lenker et al. | 606/191 |
| 6,063,111 | A * | 5/2000 | Hieshima et al. | 623/1.22 |
| 6,146,415 | A * | 11/2000 | Fitz | 606/171 |
| 6,193,686 | B1 * | 2/2001 | Estrada et al. | 604/103.09 |
| 6,241,758 | B1 * | 6/2001 | Cox | 623/1.11 |

OTHER PUBLICATIONS

EPO Publication No. EP 0 876 804 A1, "Passive Perfuson Stent Delivery System", Nov. 11, 1998.

PCT Publication No. WO 99/48908, "A Delivery Catheter", Oct. 7, 1999.

* cited by examiner

APPARATUS FOR DELIVERING ENDOLUMINAL PROSTHESES AND METHODS OF MAKING AND USING THEM

FIELD OF THE INVENTION

The present invention relates generally to apparatus and methods for delivering endoluminal prostheses within body lumens of a patient, and more particularly to apparatus for delivering tubular prostheses or "stents" within a patient's vasculature for treating stenoses or other lesions, for example, within the coronary and carotid arteries, and to methods of making and using such apparatus.

BACKGROUND

In recent years, a number of minimally invasive technologies have been developed for treating diseases, such as atherosclerosis, that result in narrowing of blood vessels, for example, within the coronary or carotid arteries. Tubular prostheses or "stents" have been developed for maintaining the patency of a blood vessel, for example, following angioplasty or other procedures used to treat a stenosis, occlusion, or other lesion within the blood vessel. The stent may be implanted across a treatment site to scaffold the site and prevent it from subsequently contracting or otherwise becoming obstructed.

Generally, the stent may be placed upon a catheter in a contracted condition, and the catheter advanced endoluminally to the treatment site until the stent is positioned across the stenosis. The stent may then be deployed and substantially anchored at the treatment site. The stent may be self-expanding, i.e., may be biased to expand to an enlarged condition upon release from the delivery catheter, thereby automatically substantially anchoring the stent at the treatment site. Alternatively, the stent may be plastically deformable, i.e., may be expanded with the aid of a balloon, which may underlie the stent on the catheter. The balloon may be inflated to expand the stent from the contracted condition to the enlarged condition wherein the stent substantially engages the wall of the treatment site. A balloon, for example, on a separate balloon catheter, may also be used to further expand and/or anchor a self-expanding stent.

Similarly, for ablation procedures and the like, a catheter including an array of electrodes, for example, on an expandable basket assembly, may be provided. The device may be introduced into a body lumen, e.g., through the patient's vasculature into the heart, to treat conditions, such as heart arrhythmia.

With any of these devices, a sheath may be provided over the catheter to protect the elements on the distal end of the catheter, such as a stent, a balloon, and/or an array of electrodes. The sheath may be advanced distally over the proximal end of the catheter until it covers the distal end and the element(s) thereon, or the distal end of the catheter may be introduced into the sheath, and advanced until it is proximate the distal end of the sheath. The distal end of the catheter, with the overlying sheath thereon, may then be introduced into a patient and positioned at a treatment site, whereupon the sheath may be retracted to expose the distal end of the catheter. After treatment, the sheath may be advanced back over the distal end of the catheter, and the entire device withdrawn from the patient.

One of the problems associated with these devices is that they may have substantially blunt distal ends that may scrape along the wall of a vessel during advancement therethrough, possibly damaging the wall and/or dislodging embolic material from the wall. To facilitate atraumatic advancement, particularly through tortuous anatomy, transition tips have been suggested for these devices.

For example, a conical or tapered nosepiece may be provided on the distal end of the catheter. A sheath may be disposed over the catheter, for example, to substantially cover the stent or other underlying element, such that the nosepiece extends distally from the end of the sheath, a distal edge of the sheath abutting the nosepiece. The nosepiece may facilitate advancement of the device through a narrow region of a blood vessel, although it may also risk catching on the wall of the vessel and/or dislodging embolic material, e.g., between the distal edge of the sheath and the nosepiece. Following delivery of a stent from the device, the nosepiece is generally positioned distal to the treated lesion. If the nosepiece is withdrawn directly, the proximal edge of the nosepiece may catch on the stent struts, resulting in the potential for trauma and embolic debris release. Alternatively, the sheath may be re-advanced across the treatment site to "recapture" the nosepiece, although in this approach the distal edge of the sheath may also catch on the stent struts.

As an alternative to a tapered nosepiece, a sheath having a rounded distal end has been suggested, as disclosed in U.S. Pat. No. 5,593,412 issued to Martinez et al. Weakened areas or slits are provided in the distal end, thereby defining sections that may be softened upon introduction of warm saline solution. Once the sections are softened, the sheath may be retracted from an underlying balloon catheter to expose and implant a stent mounted on the catheter. Introduction of saline or other liquids into a patient's vasculature, however, may be undesirable, but is necessary in order to soften the sections on the distal end of the sheath and allow the stent to be deployed from the sheath.

Another problem associated with such delivery systems is that the sheaths and/or catheters may buckle during insertion, because of the distal force applied from the proximal end to advance them through the patient's vasculature. In addition, because of their tubular nature, they may kink when advanced through tortuous anatomy, possibly damaging the device or an element within the device.

Accordingly, it is believed that delivery systems that facilitate delivery of a stent through a patient's vasculature and/or that overcome the problems discussed above would be considered useful.

SUMMARY OF THE INVENTION

The present invention is directed to apparatus for delivering treatment elements, such as tubular prostheses or "stents," within a body lumen of a patient, for example, for treating stenoses or other lesions within the coronary arteries, the carotid arteries, or other blood vessels, and to methods of making and using such apparatus.

In accordance with one aspect of the present invention, an apparatus is provided for delivering a prosthesis into a blood vessel of a patient that includes an elongate tubular member having a proximal end, a distal end, and a lumen extending between the proximal and distal ends. The distal end has a size for endoluminal insertion into a blood vessel and terminates in a substantially atraumatic distal portion including a plurality of flexible leaflets integrally molded thereto.

The leaflets are deflectable from a closed position wherein the leaflets engage one another to an open position wherein the leaflets define an opening communicating with the lumen. Preferably, the leaflets define a substantially rounded bullet shape in the closed position, although alternatively, the leaflets may define a substantially conical shape in the closed position. The leaflets are preferably substantially flexible and independently deflectable at a temperature less than body temperature, and are biased towards the closed position, but are resiliently deflectable to the open position. Adjacent leaflets may be separated by a slit, or may be connected to one another by weakened regions, the weakened regions being tearable upon retraction of the tubular member with respect to the prosthesis to allow the leaflets to be deflected towards the open position.

In a preferred embodiment, a tubular prosthesis is disposed within the lumen proximate the distal portion. An elongate bumper member having a proximal end and a distal end is also provided, the bumper member being slidably disposed within the lumen of the sheath. The distal end of the bumper member has a blunt edge disposed adjacent to the proximal end of the prosthesis for preventing axial displacement of the prosthesis upon retraction of the tubular member with respect to the bumper member and/or the prosthesis.

Preferably, the prosthesis comprises a self-expanding stent, such as a coiled-sheet stent, the stent being biased to assume an expanded condition having a cross-section larger than the lumen of the tubular member, and being compressible to a contracted condition to facilitate insertion into the lumen.

In accordance with another aspect of the present invention, an apparatus for delivering a prosthesis into a blood vessel of a patient is provided that includes an elongate tubular member, such as that described above, having a proximal end, a distal end, and a lumen extending between the proximal and distal ends, the distal end having a size for endoluminal insertion into a blood vessel. A tubular prosthesis is disposed within the lumen proximate the distal end. An elongate bumper member is also provided that includes a helical coil having a proximal end and a distal end, the bumper member being slidably disposed within the lumen of the sheath. The distal end of the bumper member has a blunt distal edge disposed adjacent a proximal end of the prosthesis for preventing axial displacement of the prosthesis upon retraction of the tubular member with respect to the bumper member.

In a preferred embodiment, the bumper member includes a helical wire compression coil, preferably a solid height coil, extending between its proximal and distal ends. A plastic bumper element extends from a distal end of the helical coil, the bumper element including the blunt distal edge thereon. An extension element extends distally from the bumper element, the extension element having a cross-section substantially smaller than the bumper element, whereby the extension element may extend through the prosthesis disposed within the lumen of the tubular member. The helical coil, bumper element, and/or the extension element include a lumen extending axially therethrough for receiving a guidewire therethrough.

In accordance with yet another aspect of the present invention, a method for making a sheath for delivering a treatment element within a body lumen of a patient is provided. A tubular member is provided that is formed from a substantially flexible material, the tubular member having a proximal end, a distal end, and a lumen extending axially between the proximal and distal ends, the distal end having a size for endoluminal insertion into a body lumen. A die is provided having a bore therein, the bore having a tapered shape. The die is heated to a temperature in excess of a melting point of the flexible material from which the tubular member is formed. The distal end of the tubular member is inserted into the bore of the heated die until a distal portion of the tubular member is softened and deformed into a tapered shape substantially enclosing the distal end. One or more slits are then created in the distal portion of the tubular member after it is deformed into the tapered shape, the slits defining a plurality of leaflets. A treatment element may be inserted into the lumen of the tubular member until it is disposed proximate the distal portion.

In a preferred method, a bullet having a tapered shape distal end is inserted into the distal end of the tubular member before inserting the distal end of the tubular member into the bore. Preferably, the bullet and the bore have corresponding substantially rounded shapes defining a mold cavity therebetween when the distal end of the tubular member is inserted into the bore.

In another preferred method, the treatment element is a tubular prosthesis for implantation within a body lumen of a patient. Preferably, the prosthesis is a self-expanding stent biased to assume an expanded condition having a cross-section larger than the lumen, and compressible to a contracted condition before being inserted into the lumen of the tubular member. The prosthesis may be inserted into the lumen of the tubular member before inserting the distal end of the tubular member into the bore, e.g., inserted into the lumen from the distal end of the tubular membrane. Alternatively, the prosthesis may be inserted into the lumen from the proximal end of the tubular member, e.g., either before or after the leaflets are formed on the distal portion of the tubular member.

An elongate bumper member may be inserted into the lumen of the tubular member, the bumper member being slidably disposed within the lumen of the tubular member, the distal end having a blunt distal edge for abutting a proximal end of the prosthesis. To make the bumper member, an elongate helical coil may be provided having a proximal end and a distal end. A tubular bumper element may be attached to the distal end of the helical coil to provide the bumper member, the bumper element including the blunt distal edge of the bumper element. Preferably, the bumper element is formed from plastic, and is attached to the helical coil by heating the bumper element until it is softened, and then directing the softened bumper element over the distal end of the helical coil. A tubular extension element may be attached to the bumper element, the extension element having a cross-section substantially smaller than the bumper element.

Other objects and features of the present invention will become apparent from consideration of the following description taken in conjunction with the accompanying drawings.

DETAILED DESCRIPTION OF THE PREFERRED EMBODIMENTS

Figure 1A:
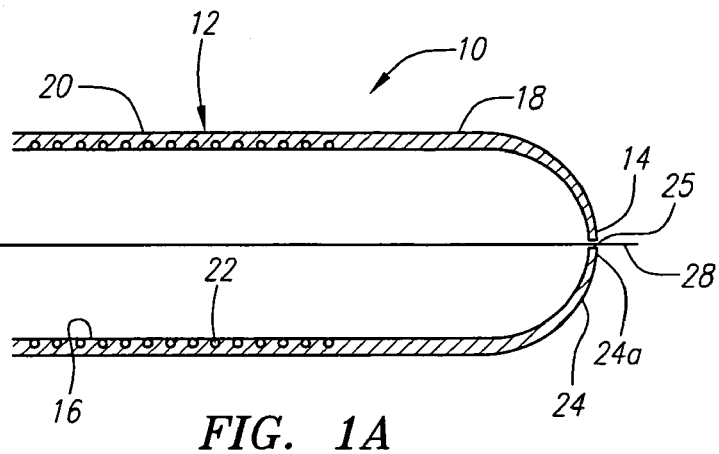
FIG. 1A is a cross-sectional side view of a sheath having a rounded distal tip, in accordance with the present invention.

Turning now to the drawings, FIGS. 1A–2B show a preferred embodiment of an apparatus 10 for delivering a stent or other tubular prosthesis 50 into a blood vessel or other body lumen of a patient (not shown). Generally, the apparatus 10 includes an elongate tubular sheath 12 having a proximal end (not shown), a distal end 14, and a lumen 16 extending generally therebetween. The tubular sheath 12 may be formed from a substantially flexible or semi-rigid material that may facilitate its advancement within a body lumen of a patient, preferably within the vasculature of a patient.

For example, the sheath 12 may be formed from a polymer, such as pebax, polyethylene, urethane, nylon, or other plastic material, that may be extruded or molded into elongate tubing of a desired length. Preferably, the tubing has a wall thickness of between about 0.003–0.006 inch (0.075–0.150 mm), and has a substantially uniform outer diameter appropriate for the size of the stent being implanted, for example, between about 1.5–2.5 mm. The sheath 12 may have a substantially uniform construction along its length, or the sheath 12 may include portions along its length having varying degrees of flexibility.

In a preferred embodiment, the sheath 12 includes a distal portion 18 formed entirely from a substantially flexible material, such as pebax, and an intermediate portion 20 formed from pebax including a stiffening element 22 therein. For for example, the intermediate portion 20 may include a braid or mesh, e.g., of stainless steel, laid over a teflon liner, with pebax tubing formed over the braid. Alternatively, the stiffening element 22 may be a helical wire coil and the like molded or otherwise formed in the tubing. The stiffening element 22 may enhance a rigidity of the intermediate portion 20, for example, to reduce the risk of the intermediate portion 20 buckling or kinking, while still providing flexibility transverse to the longitudinal axis 28, e.g., to accommodate advancement through tortuous anatomy. Preferably, the sheath 12 also includes a proximal portion (not shown) that is formed from a more rigid material, such as nylon tubing, that may include a stiffening element as described above. In a preferred embodiment, the distal portion 18 has a length of between about 10–20 cm, the intermediate portion 20 has a length of between about 20–30 cm, and the proximal portion has a length of between about 85–120 cm, more preferably about 100 cm or more.

Figure 2A:
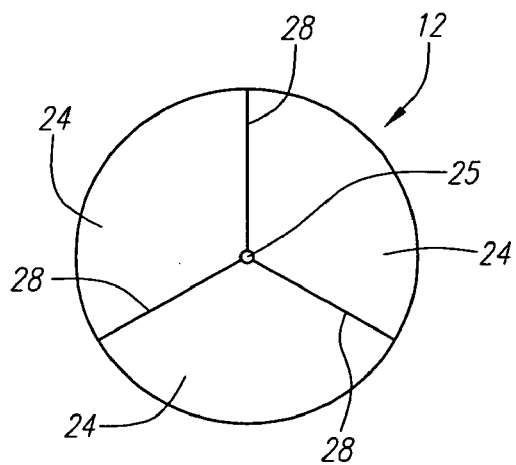
FIGS. 2A and 2B are end views of the sheath of FIGS. 1A and 1B, respectively.

The distal portion 18 of the sheath 12 preferably has a rounded bullet shape defined by a plurality of flexible leaflets 24 that are integrally formed thereon. The leaflets 24 are preferably deflectable from a closed position, wherein adjacent leaflets 24 abut one another, to an open position. In the closed position, the leaflets 24 substantially close the lumen 16, as shown in FIG. 2A. Preferably, in the closed position, the leaflets 24 define a relatively small opening 25 where their apices meet. In the open position (the leaflets 24 are shown only partially open in FIG. 2B), the leaflets 24 are spread apart to define an opening 26 communicating with the lumen 16. Preferably, in the open position, the leaflets 24 are oriented substantially axially such that the opening 26 has a cross-section similar to the lumen 16. In the preferred embodiment shown in FIGS. 2A and 2B, three leaflets 24 are provided, although additional leaflets may be provided if desired.

As best seen in FIG. 1A, in the closed position, the leaflets 24 preferably define a substantially atraumatic distal portion 18 that may facilitate advancement of the sheath 12 endoluminally within a patient's vasculature with minimal risk of dislodging embolic material from and/or otherwise damaging the wall of a body lumen through which the sheath 12 is advanced. In the preferred embodiment shown, the leaflets 24 define a substantially rounded bullet shape in the closed position. Alternatively, leaflets 24 defining a substantially conical shape (not shown) in the closed position may be provided, with the leaflets 24 preferably biased to the closed position, as described below.

The leaflets 24 are substantially flexible and independently deflectable substantially independent of the temperature to which the leaflets 24 are exposed, e.g., at a temperature substantially less than body temperature. In a preferred embodiment, the leaflets 24 are biased towards the closed position, but are resiliently deflectable to the open position. This may ensure that the opening 26 remains substantially closed until time of deployment of an element, such as stent 50, from within the lumen 16, and/or that the leaflets 24 do not catch on anything and open inadvertently. This may be particularly important when the apparatus 10 is advanced through tortuous anatomy, as described further below. Alternatively, the leaflets 24 may be at least partially plastically deformed when they are deflected from the closed position to the open position. In this alternative, the leaflets 24 may not return completely to the closed position when released from the fully open position, e.g., after the stent 50 is deployed from the apparatus 10.

Preferably, adjacent leaflets 24 are separated by a relatively narrow slit 28, although alternatively, the leaflets 24 may partially overlap with one another in the closed position. In a further alternative, adjacent leaflets may be separated by a thin-walled or weakened region (not shown) that may be easily tearable upon retraction of the sheath 12 with respect to a stent or other element being deployed from within the lumen 16. Once the weakened regions are torn, the leaflets may be freely deflected towards the open position as the element is being deployed.

Figure 1B:
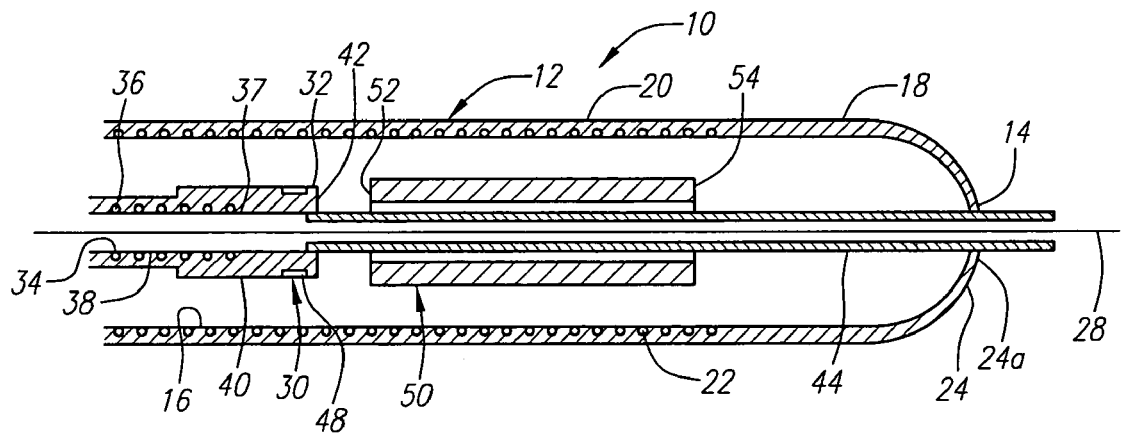
FIG. 1B is a cross-sectional side view of an apparatus for delivering a stent, including the sheath of FIG. 1A.

In addition, the leaflets 24 may have a thickness that is substantially thinner than a wall thickness of the rest of the distal portion 18, preferably tapering towards their distal tips 24a as shown in FIGS. 1A and 1B, thereby enhancing the flexibility of the leaflets 24. The tapering thickness may also ensure that the leaflets 24 are biased towards the closed position, yet may deflect easily to accommodate a guidewire (not shown), bumper extension element, and the like, as described further below.

Returning to FIG. 1B, in a preferred embodiment, the apparatus 10 also includes an elongate bumper member 30 that is slidably disposed within the sheath 12. The bumper member 30 preferably includes a proximal end (not shown), a distal end 32, and a lumen 34 that extends therebetween. The bumper member 30 preferably has a substantially uniform outer diameter slightly smaller than the interior lumen 16 of the sheath 12, preferably by about 0.003–0.005 inch (0.075–0.125 mm) to create a close sliding, but not interfering, fit between the bumper member 30 and the sheath 12. The lumen 34 has a diameter sufficiently large to accommodate a guidewire (not shown) therethrough, preferably between about 0.015–0.020 inch (0.375–0.500 mm), and more preferably about 0.016 inch (0.400 mm).

In a preferred form, the bumper member 30 is formed from a helical wire compression coil 36, e.g., having adjacent turns that substantially abut one another. The coil 36 may be formed from flat or round wire, e.g., of stainless steel and the like, that is continuously helically wound along the length of the bumper member 30, preferably a solid height coil. A relatively thin layer of teflon 38 and the like may be provided around the outside of the coil 36 to enhance a sliding relationship between the bumper member 30 and the sheath 12. Because of the coil 36, the bumper member 30 may be substantially resistant to buckling or kinking, while facilitating bending of the bumper member 30 transverse to the longitudinal axis 28.

A substantially rigid tubular segment (not shown) may be attached to or otherwise extend from the proximal end of the coil 36. Preferably, the tubular segment is a section of hypotube having an inner lumen (not shown) similar to the lumen 34 of the coil 36, and more preferably a two-stage length of hypotube that has a greater outer diameter on its proximal-most end. The tubular segment may facilitate distal advancement of the bumper member 30 into the sheath 12 with minimal risk of buckling and/or may provide enhanced tactile perception of relative movement of the bumper member 30 and the sheath 12. A valve or other seal (not shown), e.g., for accommodating a guidewire therethrough while maintaining a fluid-tight seal, may also be provided on the proximal end of the tubular segment.

The bumper member 30 also includes a tubular bumper element 40 on a distal end 37 of the coil 36 that includes a substantially blunt distal edge 42. The bumper element 40 is preferably formed from pebax or other plastic material. A plastic bumper element 40 ensures no metal-to-metal contact, e.g., between the coil 36 of the bumper member 30 and the stent 50 that may lead to corrosion of the stent material. In addition, pebax and other substantially flexible materials may deform slightly, e.g., when the sheath 12 is retracted, to enhance contact between the blunt distal edge 42 of the bumper element 40 and the stent 50. The bumper element 40 is preferably attached to the distal end 37 of the coil 36, e.g., by heating the bumper element 40 to soften it and directing it over the distal end 37, such that the bumper element is fused into the coils adjacent the distal end 37.

The bumper member 30 may also include a radiopaque or other marker 48 thereon for identifying a location of the bumper member 30 using external imaging, such as fluoroscopy. Preferably, a platinum iridium ring 48 is provided on the bumper element 40 immediately adjacent the blunt distal edge 42, thereby identifying a position of the proximal end 52 of the stent 50. Alternatively, a marker (not shown) may be provided elsewhere on the apparatus 10 in addition to or instead of the marker 48, such as on the sheath 12 or the stent 50 itself. Thus, the marker 48 may facilitate positioning of the apparatus 10, and more particularly the stent 50 or other element therein, axially within a body lumen (not shown) before deploying the element from within the sheath 12, as described further below.

The bumper member 30 may also include a tubular extension element 44 that is thermally bonded or otherwise attached to and extends distally from the bumper element 40. The extension element 44 has an outer diameter that is substantially smaller than the bumper element 40 For example, the extension element 44 may be partially inserted into the bumper element 40 as it is thermally bonded thereto so as not to interfere with the blunt edge 42 of the bumper element 40. Preferably, the extension element 44 has an outer diameter of about 0.66 mm (0.026 inch) to facilitate its insertion through the stent 50, an inner diameter of about 0.41 mm (0.016 inch) to accommodate a guidewire therethrough, and a length of about 25 mm (1.0 inch). The extension element 44 may be appropriately sized larger or smaller to accommodate a guidewire, for example, between about 0.009–0.038 in (0.225–0.95 mm). The extension element 44 is preferably substantially flexible and has a substantially smooth outer surface to provide a low-friction, sliding contact with an element disposed within the sheath 12.

In a preferred embodiment, a stent 50 or other tubular prosthesis or graft may be disposed within the lumen 16 of the sheath 12 proximate the distal portion 18. The stent 50 preferably is expandable between a contracted condition that facilitates its loading into the lumen 16 of the sheath 12, and an enlarged condition for engaging a wall of a blood vessel or other body lumen (not shown). In a preferred embodiment, the stent 50 is a coiled-sheet stent, such as that disclosed in U.S. Pat. No. 5,443,500 issued to Sigwart, and/or in co-pending application Ser. No. 09/347,845, filed Jul. 2, 1999, and Ser. No. 09/406,984, filed Sep. 28, 1999, the disclosures of which are incorporated herein by reference. The stent 50 may be self-expanding, i.e., may be biased to assume the enlarged condition, but may be compressed and constrained in the contracted condition, for example, by the lumen 16 of the sheath 12. Alternatively, the stent 50 may be plastically deformable, i.e., may be substantially relaxed in the contracted condition, but may be forcibly expanded to the enlarged condition, for example, using a balloon catheter, as is known in the art.

Figure 2B:
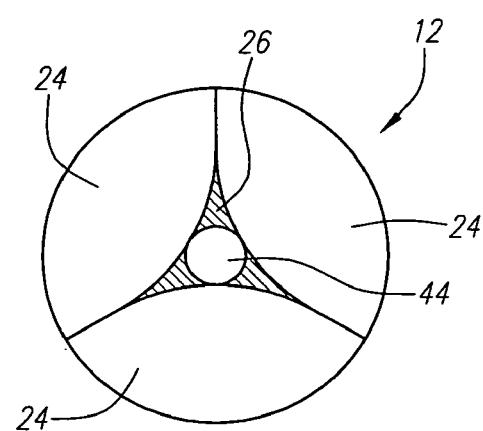

Preferably, the apparatus 10 is provided pre-assembled with the stent 50 disposed within the lumen 16 of the sheath 12 adjacent the distal portion 18 of the sheath in its contracted condition. The bumper member 30 is also disposed within the lumen 16 such that the blunt edge 42 of the bumper element 40 is adjacent a proximal end 52 of the stent 50. The extension element 44 preferably extends distally through the stent 50 and through the leaflets 24, as best seen in FIGS. 1B and 2B. The extension element 44 may facilitate insertion of a guidewire (not shown) through the apparatus 10, i.e., through the lumen 16 of the sheath 12 into the lumen 34 of the bumper member 30 to a to proximal end of the apparatus 10. Preferably, the opening 25 at the apices of the leaflets 24 accommodates the extension element 44 therethrough without causing the leaflets 24 to partially buckle or bulge.

Alternatively, the extension element 44 may be eliminated, and a guidewire inserted directly between the leaflets 24 into the lumens 16, 34. The apparatus 10 may be used to implant the stent 50 within a body lumen, preferably within a carotid artery, a coronary artery, a cerebral artery, a renal artery, or other blood vessel, as described further below. In a further alternative, the apparatus 10 may incorporate "rapid exchange" configurations where a guidewire may exit from the lumens 16, 34 of the sheath 12 and/or bumper member 30 through side ports (not shown) at a location along their lengths, i.e., at an intermediate location, rather than at their proximal ends, as is known to those skilled in the art. To accommodate a guidewire between the sheath 12 and the bumper member 30 during retraction, a longitudinal slot (not shown) may be provided in either the inner surface of the sheath or the outer surface of the bumper adjacent the side ports.

Figure 3A:
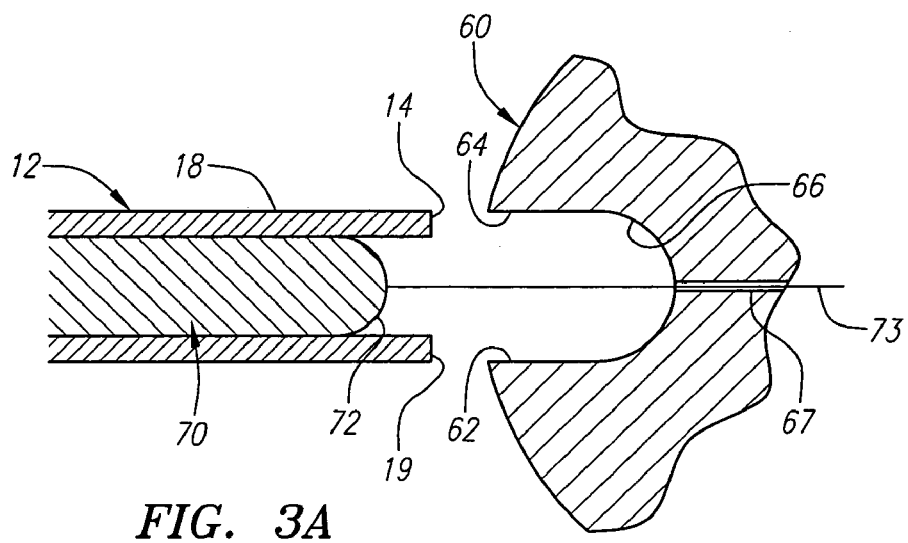
FIGS. 3A–3E are cross-sectional views showing a method for forming a rounded distal tip on a sheath, such as that shown in FIG. 1A.

Turning to FIGS. 3A–3E, a method is shown for forming a rounded bullet-shaped distal portion 18 on a tubular sheath 12 and the like. A tubular sheath 12 is provided that is formed from substantially flexible plastic material, such as those described above, preferably pebax, and that has a lumen 16 therein extending from the distal end 14 towards the proximal end (not shown). The sheath 12 initially has a distal end 14 that terminates in a substantially blunt distal edge 19 (FIG. 3A).

In a preferred embodiment, the sheath 12 has a plurality of segments having varying degrees of flexibility, for example, including a distal portion 18, an intermediate portion (not shown), and a proximal portion (also not shown). Preferably, the distal portion 18 is a predetermined length of pebax tubing that is thermal bonded, e.g., butt bonded to the intermediate portion, which is a predetermined length of pebax tubing reinforced by a stainless steel braid, such as the lengths described above. The intermediate portion, in turn, is thermally bonded to a predetermined length of nylon tubing. Alternatively, an adhesive, connectors, and the like may be used to attach two or more of the portions to one another.

Preferably, the sheath 12 is pre-assembled, i.e., with the distal, intermediate, and proximal portions bonded to one another before the distal portion 18 is formed into its bullet shape, as described below. Alternatively, the distal portion 18 may be formed into its bullet shape and/or other steps of the method performed before the distal portion 18 is attached to the intermediate portion.

A stent 50 or other prosthesis is disposed within the lumen 16, preferably a predetermined distance from the distal end 14 of the sheath 12. Preferably, the stent 50 is constrained in its contracted condition, and inserted into the distal end 14 of the sheath 12 before the distal portion 18 is formed into its bullet shape. Alternatively, the stent 50 may be provided in its contracted condition, and introduced into the lumen 16 from the proximal end of the sheath 12, e.g., either before or after the distal portion 18 is formed into its bullet shape.

In a preferred embodiment, the stent 50 is a self-expanding tubular member formed from Nitinol having a transition temperature between ambient and body temperatures. The stent 50 may be formed into its enlarged condition in its austentic phase (e.g. by hand rolling for a coiled-sheet stent) and heat treated to set the enlarged condition in its shape memory. The stent 50 may then be chilled to its martensitic phase, e.g., at a temperature below ambient temperature, and preferably between about 0–10 degrees Celsius, for example, by blowing liquid Nitrogen onto the stent 50. The stent 50 may then be pulled through one or more draw-down fixtures, i.e., tapered tubular dies (not shown), which may be chilled, to plastically compress the stent 50 into a contracted condition. In the contracted condition, the stent 50 preferably has a diameter substantially smaller than the lumen 16 of the sheath 12. The stent 50 may then be pulled from the draw-down fixture into the lumen 16 of the sheath 12. In a preferred method, a teflon tubular guide or sheath (not shown) may be used to facilitate sliding the stent 50 through one or more of the draw-down fixtures. The stent 50 may be pulled into the teflon guide as it enters a draw-down fixture, the teflon guide being split or otherwise removed from the stent 50 before it is pulled into the sheath 12.

The bumper member 30 (not shown in FIGS. 3A–3C) may be inserted into the lumen 16 of the sheath 12 until the extension element 44 approaches, but does not extend from, the distal end 14 of the sheath 12. For example, the blunt edge 42 of the bumper element 40 may abut the proximal end 52 of the stent 50, with the extension element 44 extending therethrough. Alternatively, the bumper member 30 may not be extended distally to abut the stent 50 until after the distal portion 18 is formed into its bullet shape. In a further alternative, the bumper member 30 may not be introduced into the sheath 12 until after the distal portion 18 is formed into its bullet shape.

Returning to FIGS. 3A–3C, a die 60, e.g., a spherically shaped "hot die," is provided having a bore or other recess 62 therein. The bore 62 has an entry 64 with a cross-section substantially similar to the cross-section of the sheath 12, a rounded inner end 66 having a tapered shape corresponding to the desired shape of the rounded distal portion 18 (FIG. 3C), and a relatively narrow aperture 67 extending distally from the inner end 66 through the die 60. The die 60 may be coupled to a heating element in a conventional manner such that the die 60 may be heated to a desired temperature, as is well known in the art. In a preferred method, the die 60 is heated to a temperature in excess of a melting point of the material from which the distal portion 18 of the sheath 12 is formed, for example, between about 150–200 degrees Celsius (about 300–400 degrees Fahrenheit), and preferably about 160 degrees Celsius (320 degrees Fahrenheit).

As seen in FIG. 3A, a bullet 70 is inserted a predetermined distance into the distal end 14 of the sheath 12, i.e., such that the bullet 70 does not contact the stent 50 (shown in FIG. 3B) but provides sufficient sheath material beyond a distal end 72 of the bullet 70 to form the bullet-shaped distal portion 18. Preferably, a wire or other filament 73 is attached to the bullet 70 that extends distally from the distal end 72 of the bullet 70. The bullet 70 and die 60 may be formed from like materials, preferably a hardened and polished tool steel. The distal end 72 of the bullet 70 has a predetermined curved shape corresponding to the rounded inner end 66 of the bore 62 in the die 60.

Figure 3B:
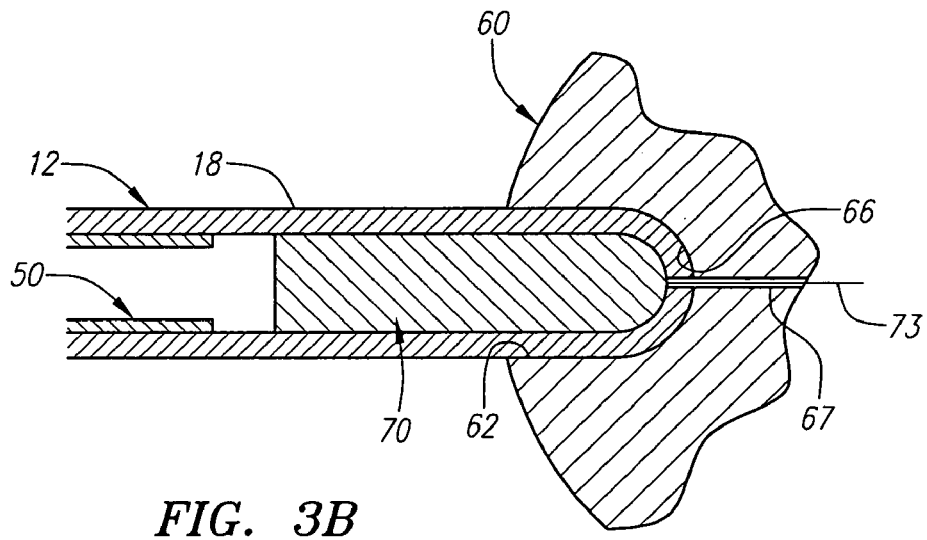

In preparation for molding the distal portion 18 of the sheath 12, the filament 73 is guided through the aperture 67, maintaining sufficient tension to keep the filament 73 taut, but without pulling the bullet 70 from the tubular member 12. As shown in FIG. 3B, the distal portion 18 of the tubular member 12 is inserted into the bore 62 of the heated die 60 until the distal portion 18 of the tubular member 12 is softened and deformed to fill the cavity defined between the distal end 72 of the bullet 70 and the rounded inner end 66 of the bore 62. Thus, the distal portion 18 is molded into a rounded bullet shape, the molded shape being defined by the distal end 72 of the bullet 70 and the rounded inner end 66 of the bore 62 in the die 60. Preferably, only slight pressure, e.g., mere hand pressure, preferably between about 1–2 pounds, is applied axially to the sheath 12 to fill the cavity defined by the bullet 70 and the bore 62 and ensure that there are no discontinuities in the resulting bullet shaped distal portion 18. Because of the filament 73, the resulting bullet shaped distal portion 18 includes the relatively small opening 25 (not shown in FIG. 3B) therethrough corresponding to the filament 73 for accommodating a guidewire or bumper extension element (not shown).

Figure 3C:
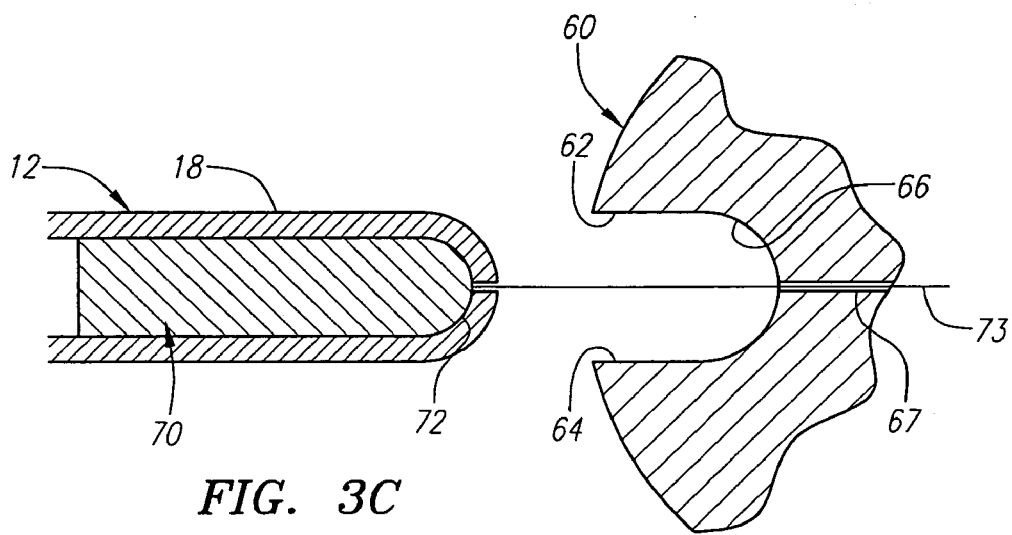

As shown in FIG. 3C, once the rounded bullet-shaped distal portion 18 is formed, the sheath 12 may be removed from the bore 62 of the die 60, and allowed to cool for sufficient time to substantially solidify the sheath, i.e., to return to its flexible, but solid state.

Figure 3D:
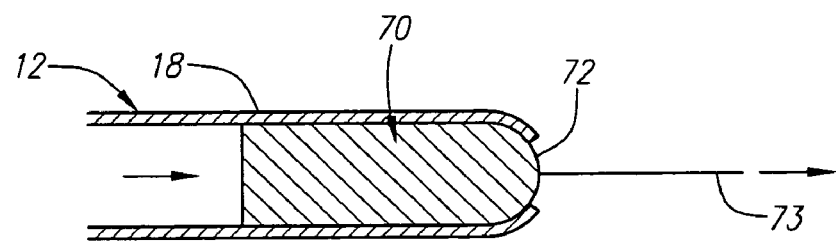
Figure 3E:
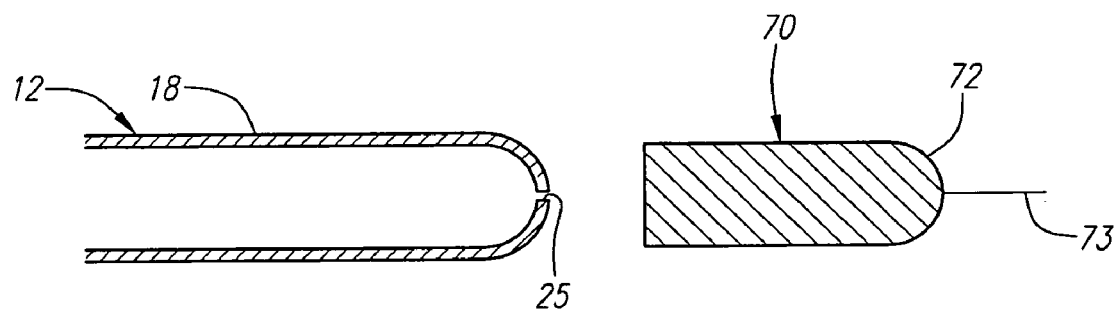

One or more slits 34 are then formed in the tapered region 22 of the distal portion 14. Preferably, a cutting device (not known) is used that includes three cutting wires or blades that are equally spaced radially about a central axis. The cutting device is aligned with the longitudinal axis 28 of the sheath 12 and forced into the enclosed distal portion 18 until the cutting device cuts completely through the material of the enclosed distal portion 18. The cutting device is then withdrawn, thereby providing a plurality of substantially independently flexible leaflets 24 on the distal portion 18. As shown in FIG. 3D, the bullet 70 may then be removed from the distal portion 18, e.g., by pulling on the filament 73 to deflect the leaflets 24 and withdraw the bullet 70 through the opening 26. The leaflets 24 preferably resiliently return to their closed position upon removal of the bullet 70, as shown in FIG. 3E, thereby defining the opening 25.

Alternatively, the filament 73 and aperture 67 may be eliminated from the bullet 70 and die 60, and the bullet 70 withdrawn from the formed sheath 12 using other methods. For even numbers of slits, a cutting device including a single blade or wire (not shown) may be oriented substantially perpendicular to the longitudinal axis 28 of the sheath 12, and a plurality of individual transverse slits may be cut into the distal portion 18. In alternative methods, individual leaflets may be formed using a multi-cavity tool, and the leaflets may be shaped into a final position, as will be appreciated by those skilled in the art.

Once the leaflets 24 are formed, the bumper member 30 may be advanced further distally to push the stent 50 into a desired position within the lumen 16 of the sheath 12, i.e., proximate the bullet-shaped distal portion 18, and/or to direct the extension element 44 through the opening 25. To facilitate this pre-loading stage, it may b desirable to form the distal portion 18 of the sheath 12 from a substantially transparent material, thereby facilitating visual monitoring of the stent 50 and/or the bumper member 30. The apparatus 10 is then ready to be used to introduce and implant the stent 50 within a body lumen of a patient, as described further below.

In an alternative method, the stent 50 may be inserted into the sheath 12 from its proximal end after distal portion 18 is formed into its bullet shape. For example, the stent 50 may be constrained in its contracted condition, and advancing it through the lumen 16 of the tubular member 12 to the distal portion 18. The stent may be released, i.e., unconstrained, once introduced into the lumen 16, whereupon the stent may partially expand to engage the wall of the lumen 16. Preferably, the stent remains slidable within the lumen 16 such that the stent 50 may be advanced to a location proximate the distal portion 18 and/or easily deployed through the opening 26. The bumper member 30 may be inserted into the proximal end of the sheath 12 and directed distally to advance the stent 50 to the desired position.

Figure 4A:
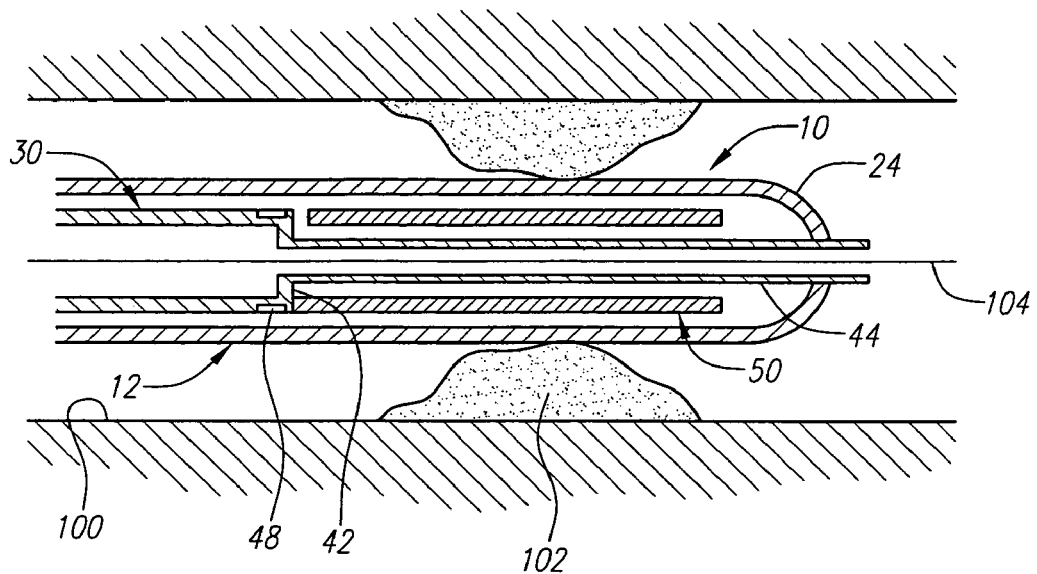
FIGS. 4A and 4B are cross-sectional views of a body lumen, showing a method for implanting a stent using an apparatus in accordance with the present invention.
Figure 4B:
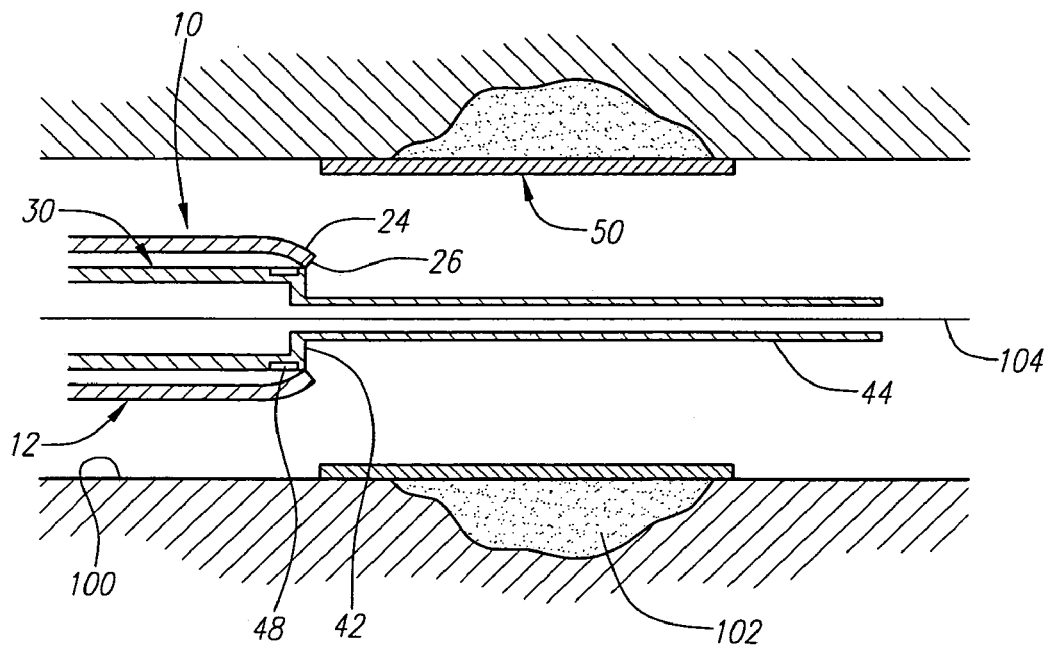

Turning to FIGS. 4A and 4B, the apparatus 10 may be used to implant the stent 50 or other prosthesis within a body lumen 100 of a patient, such as within a coronary, carotid, cerebral, renal artery, or other blood vessel. The apparatus 10 is percutaneously introduced into the patient's vasculature and advanced distally to a target treatment region 102. Preferably, the apparatus 10 is advanced over a guidewire 104 already placed across the treatment region 102 using conventional methods. The guidewire 104 may be backloaded through the extension element 44, and through the bumper member 30 to its proximal end (not shown).

The rounded distal portion 18 of the sheath 12 substantially protects the stent 50 during advancement and/or allows atraumatic advancement of the apparatus 10. Preferably, as explained above, the leaflets 24 are resiliently flexible and biased to the closed position, causing the leaflets 24 to hug the guidewire 104 during advancement, particularly through tortuous anatomy. For example, if the leaflets 24 are flexible and biased to the closed position, the leaflet(s) 24 on the outside of a sharp bend may hug the guidewire 104, rather than deflecting away from the guidewire 104 and risking catching on the wall of the vessel, and possibly damaging the wall and/or dislodging embolic material from the wall. In addition, the rounded distal portion 18 may facilitate advancement of the apparatus 10 through the treatment region 100.

Once the apparatus 10 is advanced into the body lumen 100, the stent 50 is positioned across the treatment region 102, as shown in FIG. 4A, for example, by monitoring the marker 48 using fluoroscopy and the like. Preferably, the treatment region 102 is a stenotic or occluded region of a blood vessel, although other lesions or damaged vessel segments may be treated, as will be appreciated by those skilled in the art. Once the stent 50 is properly positioned, the bumper member 30 is held stationary, and the sheath 12 withdrawn to deploy the stent 50 from the lumen 16, as shown in FIG. 4B. Because of their flexible nature, the leaflets 24 easily deflect outward to allow the stent 50 to be deployed through the opening 26, and slide over the stent 50 and/or over the bumper member 30. Once the stent 50 is deployed, the apparatus 10 may be withdrawn from the body lumen 100 and from the patient (not shown). Preferably, the sheath 12 remains in its retracted position without requiring advancement back over the bumper element 40 and/or the extension element 44 before removal of the apparatus 10. The leaflets 24 preferably hug the outside of the bumper member 30, thereby facilitating substantially atraumatic withdrawal of the apparatus 10.

Preferably, the stent 50 is self-expanding, and therefore automatically expands upon deployment to engage the body lumen 100 at the treatment location 102. The stent 50 may trap embolic material between itself and the body lumen 100 and/or may dilate and hold the body lumen 100 open. If desired to further expand the stent 50, an expansion device, such as a catheter (not shown) may be introduced into the body lumen 100, e.g., upon removal of the apparatus 10, and positioned within the stent 50. A balloon or other expandable member on the catheter may be expanded to engage and further expand the stent 50 to a predetermined diameter, e.g., corresponding substantially to the unobstructed diameter of the body lumen 100.

In an alternative embodiment (not shown), the stent 50 may be plastically expandable, and may be mounted onto a catheter that is inserted into a sheath 12 in accordance with the present invention. The catheter may include a balloon or other expandable member over which the stent may be mounted. Once the sheath is retracted to deploy the stent, for example, at a target treatment region, the expandable member may be expanded, e.g., by inflating the balloon, to plastically deform the stent and expand it to engage the body lumen at the treatment region. Once the stent has been expanded to a desired size, the expandable member may be deflated, and the apparatus withdrawn from the body lumen and the patient.

In further alternatives, other deployable devices may be provided within a sheath in accordance with the present invention, such as an electrode device, e.g., an array of electrodes on an expandable basket assembly and the like. Once a desired location is reached, such as a chamber of a heart, the sheath may be retracted with respect to the underlying device, until one or more elements on the device are deployed from the sheath. A procedure may be completed at the location, e.g., an ablation procedure, and then the sheath and device may be withdrawn from the location.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the spirit and scope of the appended claims.

What is claimed is:

1. An apparatus for delivering a prosthesis into a blood vessel of a patient, comprising:
    an elongate tubular member having a proximal end, a distal end, and a lumen extending between the proximal and distal ends, the distal end having a size for endoluminal insertion into a blood vessel and terminating in a substantially atraumatic distal portion comprising a plurality of flexible leaflets integrally molded thereto, the leaflets being deflectable from a closed position wherein the leaflets engage one another to an open position wherein the leaflets define an opening communicating with the lumen;

a tubular prosthesis disposed within the lumen proximate the distal portion; and an elongate bumper member having a proximal end and a distal end, the bumper member being slidably disposed within the lumen of the elongate tubular member, the distal end of the bumper member having a blunt edge that engages the proximal end of the prosthesis for preventing axial displacement of the prosthesis upon retraction of the tubular member with respect to the bumper member;

wherein the bumper member comprises a helical coil.

2. An apparatus for delivering a prosthesis into a blood vessel of a patient, comprising:

an elongate tubular member having a proximal end, a distal end, and a lumen extending between the proximal and distal ends, the distal end having a size for endoluminal insertion into a blood vessel;

a tubular prosthesis disposed within the lumen proximate the distal end; and an elongate bumper member comprising a helical coil having a proximal end and a distal end, the bumper member being slidably disposed within the lumen of the elongate tubular member, the distal end of the bumper member having a blunt distal edge that engages the proximal end of the prosthesis for preventing axial displacement of the prosthesis upon retraction of the tubular member with respect to the bumper member.

3. The apparatus of claim 2, wherein the tubular member comprises a substantially atraumatic distal portion comprising a plurality of flexible leaflets integrally molded thereto, the leaflets being deflectable from a closed position wherein the leaflets engage one another to an open position wherein the leaflets define an opening communicating with the lumen.

4. The apparatus of claim 3, wherein the leaflets define a substantially rounded bullet shape in the closed position.

5. The apparatus of claim 3, wherein the leaflets are substantially flexible and independently deflectable at a temperature less than body temperature.

6. The apparatus of claim 3, wherein the leaflets are biased towards the closed position, but are resiliently deflectable to the open position.

7. The apparatus of claim 2, wherein adjacent leaflets are connected to one another by weakened regions, the weakened regions being tearable upon retraction of the tubular member with respect to the prosthesis to allow the leaflets to be deflected toward the open position.

8. The apparatus of claim 3, wherein the leaflets include a portion having a thickness that is substantially thinner than a wall thickness of the distal portion of the tubular member from which the leaflets extend.

9. The apparatus of claim 2, wherein the bumper member comprises a helical wire compression coil extending between its proximal and distal ends.

10. The apparatus of claim 2, wherein the bumper member comprises a plastic bumper element extending from a distal end of the helical coil, the bumper element including the blunt distal edge thereon.

11. The apparatus of claim 10, wherein the bumper member further comprises an extension element extending from the bumper element, the extension element having a cross-section substantially smaller than the bumper element, whereby the extension element may extend through the prosthesis disposed within the lumen of the tubular member.

12. The apparatus of claim 11, wherein the extension element comprises a lumen for receiving a guidewire therethrough.

13. The apparatus of claim 2, further comprising a radiopaque marker on the distal end of the bumper member.

* * * * *